United States Patent [19]

Lyons

[11] Patent Number: 5,073,383

[45] Date of Patent: Dec. 17, 1991

[54] INHIBITING AGGREGATION IN FLUOROCARBON EMULSIONS

[75] Inventor: Robert T. Lyons, Cary, N.C.

[73] Assignee: Affinity Biotech, Inc., Boothwyn, Pa.

[21] Appl. No.: 341,444

[22] Filed: Apr. 21, 1989

[51] Int. Cl.$^5$ .................. A61K 33/42; A61K 31/025
[52] U.S. Cl. ..................................... 424/606; 514/78;
  514/755; 514/756; 514/759
[58] Field of Search ................. 424/606; 514/78, 755, 514/756, 759

[56] References Cited

U.S. PATENT DOCUMENTS

| | | | |
|---|---|---|---|
| 2,145,344 | 1/1939 | Draisbach | 424/606 |
| 4,186,253 | 1/1980 | Yokoyama et al. | 514/759 |
| 4,402,984 | 9/1983 | Moore | 514/755 |
| 4,423,077 | 12/1983 | Sloviter | 514/759 |
| 4,942,179 | 7/1990 | Borgarello et al. | 514/759 |

Primary Examiner—Mukund J. Shah
Assistant Examiner—E. C. Ward
Attorney, Agent, or Firm—J. Edward Hess; Donald R. Johnson; Stanford M. Back

[57] ABSTRACT

Aggregation of fluorocarbon emulsion particles, which occurs when the emulsion mixes with blood, is reduced by the addition of relatively large amounts of phosphate.

11 Claims, No Drawings

INHIBITING AGGREGATION IN FLUOROCARBON EMULSIONS

BACKGROUND OF THE INVENTION

Perfluorocarbon (PFC) emulsions as substitutes for blood in oxygen transport are well-known. It is also well known that they should have small particle size, i.e., the perfluorocarbon should be less than 200 nanometers (0.2 micron), to enable the perfluorocarbon particles, which carry the oxygen, to pass through the smallest arteries in the body.

A problem with typical fluorocarbon emulsions is an adverse reaction that occurs when they mix with normal blood, as inevitably occurs when such emulsions are substituted for blood. It is not usually intended for such a substitution to be a complete, 100% exchange. Indeed, an absolute, 100%, exchange would be difficult to achieve even if it were intended.

The problem is that the emulsion particles tend to aggregate in the presence of blood. They do not coalesce to form a single larger particle out of several smaller ones, rather smaller particles gather together in clusters. Just like larger particles, the clusters do not pass through smaller arteries as well, which reduces oxygen transport, and they increase emulsion viscosity as well, which also impedes oxygen transport by reducing arterial flow.

SUMMARY OF INVENTION AND PRIOR ART

We have found that the inclusion of relatively high concentrations of phosphate in the emulsion reduces or delays this aggregation problem. Although the use of phosphate-containing saline solutions as the aqueous phase of perfluorocarbon emulsions is known (see e.g., Sloviter, U.S. Pat. No. 4,423,077), such uses have generally been for pH control and been on the order of 1-2 millimoles per liter of aqueous phase, usually even less. U.S. Pat. No. 4,186,253 discloses the use of large amounts of phosphate but in a perfusion context, organ preservation, which does not have the same problems as with in vivo applications and which normally involves no contact with the blood at all.

The invention is applicable to the perfluorocarbon emulsions known in the prior art for oxygen transport in medical applications. These emulsions comprise water, which may or may not contain conventional blood salts such as Tyrode's or Ringer's solution, perfluorocarbon and surfactant.

The perfluorocarbon in the emulsion is generally a perfluorocyclocarbon, i.e., a cyclic compound of carbon which may or may not contain acyclic or alkyl side chains, preferably lower alkyl ($C_1$-$C_4$) side chains. The compound may be mono, di or polycyclic, as with cyclohexane or naphthalene and phenanthrene derivatives but usually has no more than 4 rings, preferably 2-3. The description of cyclocarbon as perfluoro means that all or almost all of the hydrogen atoms, usually at least 80%, preferably at least 90%, have been replace with fluorine. For effective use as a blood substitute the cyclocarbon usually has 9-12 carbon atoms.

Typical compounds of the type described above are perfluoro trimethylcyclohexane, isopropylcyclohexane, tetramethylcyclohexane, 1-methyl-4-isopropylcyclohexane, n-butylcyclohexane, decahydroacenaphthene, decalin, methyl and dimethyldecalins, tetradecahydrophenanthrene, dodecahydrofluorene, and diisopropylcyclohexane.

Preferred cyclocarbons are non-aromatizable polycyclic perfluoro compounds having two bridgehead carbon atoms linked through a bridge containing at least one carbon atom. By the term bridgehead carbon atom is meant a carbon atom bonded to three other carbons in a cyclic compound having 2 or more rings. By the term "non-aromatizable" is meant a polycyclic perfluoro compound whose ring structure cannot be aromatized without destruction of its original carbon-to-carbon cyclic bonds. These preferred compounds are distinguished from perfluorodecalin and others mentioned above which can be aromatized. Examples of these preferred compounds are the perfluoro derivatives of such $C_9$-$C_{12}$ polycyclic compounds as bicyclononanes (e.g. bicyclo[3.3.1]nonane, 2,6-dimethylbicyclo[3.3.1]nonane or 3-methylbicyclo[3.3.1]nonane), adamantane, methyl and dimethyladamantane, ethyladamantane, tetrahydroicyclopentadiene, methyl and dimethylbicyclo-octanes, pinane, camphane, 1,4-6, 9-dimethanodecalin, bicyclo[4.3.2]undecane, bicyclo[5.3.0]-decane and the like, or mixtures thereof. They can be made by known means. Compounds of this preferred type are described in U.S. Pat. No. 4,105,798 which is incorporated herein by reference.

Certain acyclic perfluorocarbons have also been used as blood substitutes, most notably perfluorotributylamine.

The surfactants used to disperse the perfluorocarbon in the aqueous phase are usually non-ionic such as the polyoxyethylenes and propylenes available commercially as "Pluronics," preferably "Pluronic F-68". However, the Pluronics are not as good from a toxicity standpoint as the phospholipids, preferably lecithin, which is egg yolk phospholipid. Other non-toxic surfactants have also been used.

The amount of perfluorocarbon in the emulsion is usually 10-50 volume percent, more frequently 10-30 percent. The amount of surfactant is usually 1-10% (w/v) preferably 2-6% (w/v). The expression % (w/v) means the number of grams of surfactant in 100 cc. of emulsion.

The amount of phosphate added is at least 15 millimoles (mM.) $PO_4$ per liter of water, generally 10-50, preferably 20-40, more preferably 20-30. It is desirable to keep the amount as low as possible, while still inhibiting aggregation, because if too high, emulsion viscosity may increase and/or there may be some incompatibility with annex salt solutions. The phosphate concentration can be optimized by compatibility studies with blood either in vivo or ex vivo.

The phosphate can be in the form of any non-injurious pharmaceutically acceptable salt such as potassium, sodium, ammonium, etc. It can be also the mono or dihydrogen salts or mixtures thereof.

I have found that the protective effect of the phosphate against aggregation is not achieved if the phosphate is added to finished, sterile emulsion. The phosphate salts must be present before sterilization. In this respect, the usual procedure for making a PFC emulsion is to form a pre-mix of the surfactant add water, and PFC. mix, homogenize or otherwise reduce the particle size to less than 0.5 micron. filter, bottle and finally heat sterilize. The phosphate should be added prior to sterilization and is preferably present during the homogenization step, as by being included in the water employed in the pre-mixing.

EXAMPLE

A perfluorocarbon emulsion containing 25% PFC (w/v), 2.4% (w/v) with egg phospholipid emulsifier, and the balance water is prepared with the aid of a Gaulin homogenizer. The PFC is a mixture of F-methyladamantane, F-bicyclodimethylnonane and other F compounds, as is obtained by the fluorination of methyladamantane with $CoF_3$, generally as in Example 2 of U.S. Pat. No. 4,105,798. The particle size of the emulsion is under 0.5 micron. The emulsion is identified as S-168.

Another emulsion is prepared in the same manner except that the water used in preparing the emulsion contains $KH_2PO_4$, $NaH_2PO_4.H_2O$, and $Na_2HPO_4.7H_2O$ in amounts of 1.1, 9.3, and 14.7mm $PO_4$/l $H_2O$, respectively, for a total of 25.1 mm $PO_4$/l $H_2O$. This emulsion is identified at S-171.

The agglomeration characteristics of the above emulsions is determined as follows:

Sprague—Dawley rats are infused with 20 ml/kg of the emulsion through the tail vein. At various times after infusion, blood samples are withdrawn from the rats with a syringe containing 50 microliters per ml of blood of a 10% solution of the anticoagulant, ethylenediamine tetraacetic acid disodium salt.

The withdrawn samples are examined under a video microscope (1000X) and the results noted. To understand the results reported below, the following background information is helpful.

With no aggregation, whether or not in the presence of blood, the emulsion particles appear as single particles. The onset of aggregation is seen by a few particles clustering together. The diameter of the cluster can be visually compared to that of the nearby red blood cells (7 microns). As agglomeration continues, the cluster size is observed and reported as a multiple of red blood cell diameter.

The data on S-168 and S-171 are as follows:

| Time After Infusion | S-168 (no $PO_4$) | S-171 (with $PO_4$) |
| --- | --- | --- |
| 30 Minutes | single particles | single particles |
| 1.5 Hours | small aggregates starting to appear much smaller than red blood cells | single particles |
| 3 Hours | massive aggregation 5-10X red blood cells | single particles |
| 4 Hours | worse than at 3 hours blood platelets appear trapped in aggregates | some aggregates each equal in diameter to one red cell |
| 24 Hours | No further observation | massive aggregation made in view of 4 hour results |

It is apparent from the above that the $PO_4$-containing emulsion was much more aggregation resistant than the emulsion without $PO_4$. The same effect is observed with human blood. Although it is apparent from the data that aggregation is delayed and not prevented absolutely, delay for 2–3 hours is often a satisfactory solution, since the medical purpose will be accomplished and the emulsion removed within the delay period anyway.

The invention claimed is:

1. Method of inhibiting aggregation in aqueous perfluorocarbon emulsion in contact with blood which comprises incorporating phosphate in a physiologically acceptable the emulsion in amount of at least 15 mM phosphate per liter of water contained in the emulsion, effective to inhibit said aggregation.

2. Method according to claim 1 wherein the amount of phosphate is 20–50 mM.

3. Method according to claim 1 or 2 wherein the amount of perfluorocarbon is 10–30%.

4. Method according to claim 1 or 2 wherein the perfluorocarbon is a perfluoroadamantane or perfluoropolymethylbicyclononane.

5. In a process in which a sterilized perfluorocarbon emulsion is contacted intraveneously with blood, the improvement which comprises inhibiting aggregation of perfluorocarbon particles in the emulsion by adding phosphate to the emulsion in a physiologically acceptable amount of at least 15 mM per liter of water contained therein.

6. Method according to claim 5 wherein the amount of phosphate is 20–50 mM.

7. Method according to claim 5 or 6 wherein the amount of perfluorocarbon is 10–30%.

8. Method according to claim 5 or 6 wherein the perfluorocarbon is a perfluoroadamantane or perfluoropolymethylbicyclononane.

9. Method according to claim 5 or 6, wherein the phosphate is added prior to the sterilization of the emulsion.

10. A blood substitute composition comprising a sterilized perfluorocarbon emulsion containing (a) water, (b) 10–50% perfluorocarbon, (c) surfactant and (d) a physiologically acceptable amount of at least 15 mM per liter of water of pharmaceutically acceptable phosphate salts added to said water prior to the sterilization of said emulsion; said composition being substantially free of aggregation for two hours with the blood being substituted.

11. Method according to any of claims 1 or 2 wherein the amount of perfluorocarbon is 10–50%.

* * * * *

UNITED STATES PATENT AND TRADEMARK OFFICE
CERTIFICATE OF CORRECTION

PATENT NO. : 5,073,383

DATED : December 17, 1991

INVENTOR(S) : Robert T. Lyons

It is certified that error appears in the above-identified patent and that said Letters Patent is hereby corrected as shown below:

Column 4,
Claim 1, lines 19 and 20 should read: --comprises incorporating phosphate in the emulsion in a physiologically acceptable amount of at least 15 mM--

Signed and Sealed this

Twenty-fourth Day of August, 1993

Attest:

BRUCE LEHMAN

Attesting Officer    Commissioner of Patents and Trademarks